United States Patent
Smith et al.

(10) Patent No.: US 9,295,205 B2
(45) Date of Patent: Mar. 29, 2016

(54) SYSTEM FOR PRODUCING A BIOGAS

(71) Applicant: SSB International, LLC, Mays Landing, NJ (US)

(72) Inventors: Michael J. Smith, Mays Landing, NJ (US); Edward William Gaine, Dorothy, NJ (US)

(73) Assignee: SSB International, LLC, Mays Landing, NJ (US)

( * ) Notice: Subject to any disclaimer, the term of this patent is extended or adjusted under 35 U.S.C. 154(b) by 73 days.

(21) Appl. No.: 14/204,261

(22) Filed: Mar. 11, 2014

(65) Prior Publication Data

US 2014/0193898 A1    Jul. 10, 2014

Related U.S. Application Data

(63) Continuation of application No. 13/094,112, filed on Apr. 26, 2011, now abandoned.

(60) Provisional application No. 61/343,205, filed on Apr. 26, 2010.

(51) Int. Cl.

| | |
|---|---|
| *C12N 5/00* | (2006.01) |
| *C12N 5/02* | (2006.01) |
| *A01G 31/06* | (2006.01) |
| *C12N 1/12* | (2006.01) |
| *C12P 5/02* | (2006.01) |
| *C12M 1/107* | (2006.01) |

(52) U.S. Cl.
CPC ............... *A01G 31/06* (2013.01); *C12M 21/04* (2013.01); *C12N 1/12* (2013.01); *C12P 5/023* (2013.01); *Y02E 50/343* (2013.01)

(58) Field of Classification Search
CPC ......... A01G 31/06; C12M 21/04; C12N 1/12; C12P 5/023; Y02E 50/343
See application file for complete search history.

(56) References Cited

U.S. PATENT DOCUMENTS

| | | | |
|---|---|---|---|
| 4,699,632 A | 10/1987 | Babu et al. | |
| 7,951,296 B2 | 5/2011 | Williams | |
| 2003/0138365 A1* | 7/2003 | Obidniak et al. | ............ 422/224 |
| 2007/0094926 A1 | 5/2007 | Branson et al. | |
| 2009/0321349 A1 | 12/2009 | Offerman et al. | |
| 2010/0223839 A1 | 9/2010 | Garcia-Perez et al. | |

OTHER PUBLICATIONS

Wagner, "Azolla: A Review of Its Biology and Utilization," Botanical Review, vol. 63, No. 1, pp. 1-26 (1997).

Cantrell et al, "Livestock waste-to-bioenergy generation opportunities," Bioresource Technology, vol. 99, pp. 7941-7953 (2008).

Wang et al, "$CO_2$ bio-mitigation using microalgae," Applied Microbiology and Biotechnology, vol. 79, pp. 707-718 (2008).

Haidue et al, "SunCHem: an integrated process for the hydrothermal production of methane from microalgae and $CO_2$ mitigation," Journal of Applied Phycolology, vol. 21, pp. 529-541 (2009).

Jain et al, "Production of biogas from aquatic biomass: a comparison with terrestrial biomass," Research and Industry, vol. 35, pp. 104-107 (Jun. 1990).

Office Action issued Feb. 4, 2013 in U.S. Appl. No. 13/094,112 by Smith.

Office Action issued Sep. 13, 2013 in U.S. Appl. No. 13/094,112 by Smith.

* cited by examiner

*Primary Examiner* — Annette Para

(74) *Attorney, Agent, or Firm* — Panitch Schwarze Belisario & Nadel LLP

(57) ABSTRACT

A method for producing a biogas is provided. The method includes the steps of providing a polyculture of aquatic plants to a growth system; continuously providing water, carbon dioxide, air and nutrients to the polyculture contained within the growth system; growing the polyculture for a time sufficient to produce an aquatic plant-based biomass; withdrawing a portion of the aquatic plant-based biomass contained within the growth system; and treating the withdrawn aquatic plant-based biomass to produce a biogas.

8 Claims, 5 Drawing Sheets

SYSTEM FOR PRODUCING A BIOGAS

CROSS-REFERENCE TO RELATED APPLICATIONS

This application is a continuation of U.S. patent application Ser. No. 13/094,112, filed Apr. 26, 2011, which claims the benefit of U.S. Provisional Application No. 61/343,208, filed Apr. 26, 2010, the entire contents of which are incorporated by reference herein.

BACKGROUND OF THE INVENTION

The present invention relates to the production of synthetic fuels, also known as synfuels, and, more particularly, to the production of a plant-based and methane-containing biogas. Biogas can be obtained or produced from various organic or agricultural matter and is useful as a low-cost fuel for heating or energy production purposes. However, the production of biogases can often be costly and can result in waste products and exhaust gases that require further treatment and/or disposal.

Accordingly, it is desirable to provide a method for producing a biogas which is efficient, sustainable, and which results in a minimal amount of waste products.

BRIEF SUMMARY OF THE INVENTION

Briefly stated, in one embodiment, the present invention is directed to a method for producing a biogas. The method comprises the steps of providing a polyculture of aquatic plants to a growth system; continuously providing water, carbon dioxide, air and nutrients to the polyculture contained within the growth system; growing the polyculture for a time sufficient to produce an aquatic plant-based biomass; withdrawing a portion of the aquatic plant-based biomass contained within the growth system; and treating the withdrawn aquatic plant-based biomass to produce a biogas.

According to another embodiment, the present invention is directed to a system for producing a biogas. The system comprises a plurality of growing trays containing water and a polyculture, the plurality of growing trays being configured to continuously receive water, carbon dioxide, air and nutrients until a biomass is produced; a harvesting system configured to harvest a portion of the biomass contained in at least one of the plurality of growing trays; and a gasifier comprising a pyrolysis chamber and a combustion chamber. The pyrolysis chamber and the combustion chamber are seperately arranged such that the pyrolysis chamber is arranged within an interior of the combustion chamber.

Another embodiment of the present invention relates to a method for producing electricity. The method comprises the steps of providing a polyculture of aquatic plants to a growth system; continuously providing water, carbon dioxide, air and nutrients to the polyculture contained within the growth system; growing the polyculture for a time sufficient to produce an aquatic plant-based biomass; withdrawing a portion of the aquatic plant-based biomass contained within the growth system; treating the withdrawn aquatic plant-based biomass to produce a biogas; and combusting the biogas in an internal combustion engine.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there are shown in the drawing embodiments which are presently preferred. It should be understood, however, that the invention is not limited to the precise arrangements and instrumentalities shown.

In the drawings

DETAILED DESCRIPTION OF THE INVENTION

Figure 1:
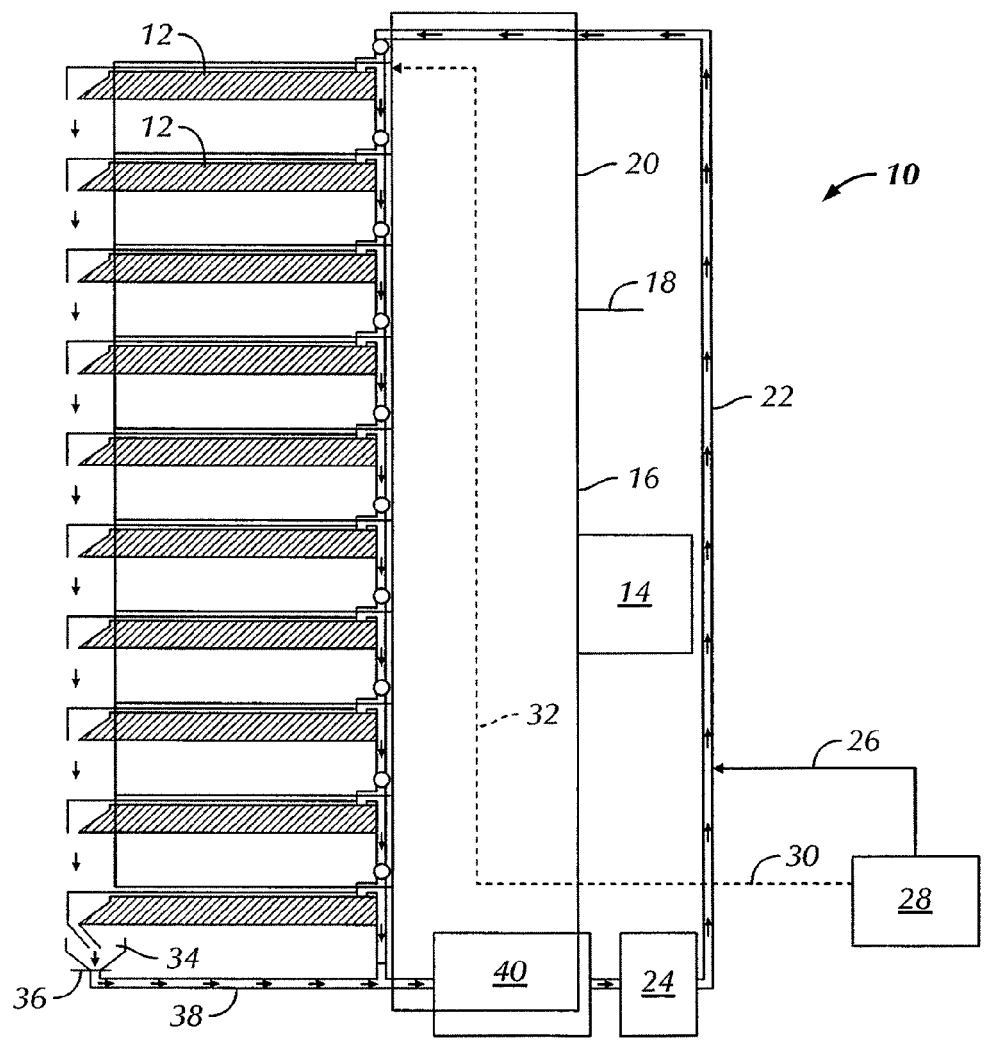
FIG. 1 is a schematic block diagram illustrating a growth system for growing a polyculture according to preferred embodiment of the present invention.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the system and designated parts thereof. Unless specifically set forth herein, the terms "a", "an" and "the" are not limited to one element but instead should be read as meaning "at least one". The terminology includes the words noted above, derivatives thereof and words of similar import.

Figure 3:
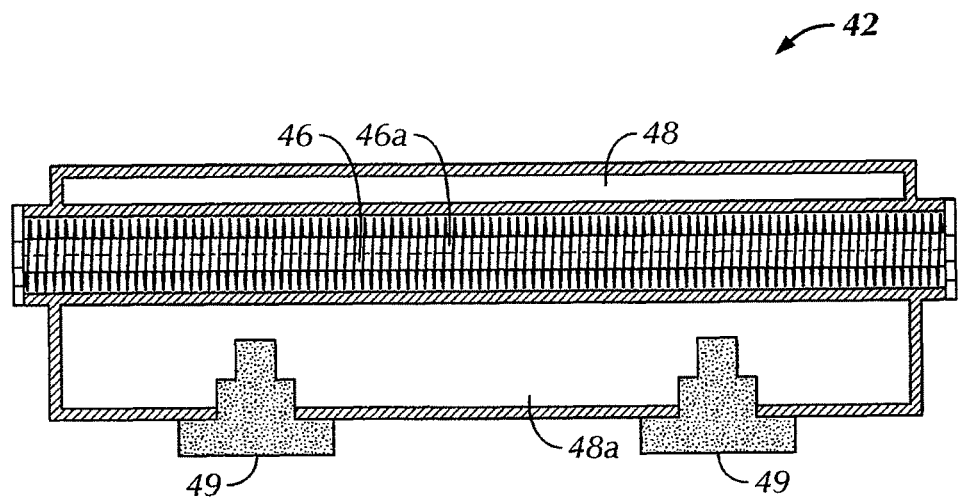
FIG. 3 is a cross-sectional side elevation view of a gasifier according to a preferred embodiment of the present invention.
Figure 4:
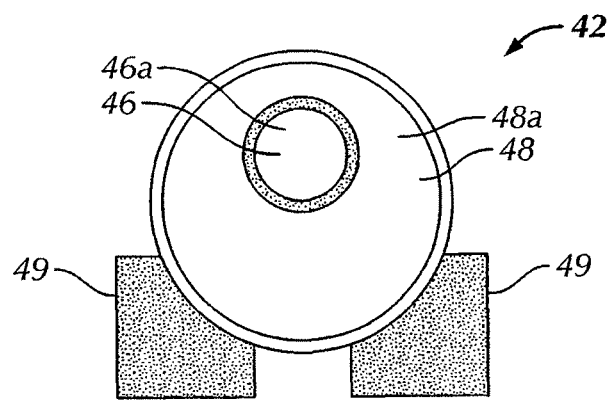
FIG. 4 is an end elevational view of the gasifier shown in FIG. 3.

Referring to the drawings in detail, wherein like numerals and characters indicate like elements throughout, there is shown in FIG. 1 a growth system 10 in accordance with a preferred embodiment of the present invention. With reference to FIGS. 3-4, there is shown a gasifier 42 in accordance with a preferred embodiment of the present invention.

The present invention relates to a system and method for producing products that may be utilized as fuels from cultivated duckweed. It will be understood by those skilled in the art that the products produced from the below described process may be utilized for various other purposes. More particularly, the present invention relates to a method for producing a biofuel.

The method comprises combining air, carbon dioxide, water and nutrients required for growth and cultivation of a polyculture based mainly on aquatic plant life. Specifically, the starting polyculture contains multiple types of aquatic plants. More preferably, the starting polyculture contains at least one species of duckweed, and preferably also contains at least one species of a cyanobacteria, which is a green algae, and an aquatic fern. The preferred species of duckweed include *Lemna minor* and species belonging to the genera *Spirodela*, *Wolffiella* and *Wolffia*. Other examples of plants that may be used include, but are not limited to, any plants of the Lemnoideae or Lemnaceae families. More preferably, the polyculture contains multiple species of duckweed, particularly *Lemna minor* and species belonging to the genera *Spirodela* and *Wolffiella*. The aquatic fern of the polyculture is preferably species of the genus *Azolla*. The cyanobacteria is preferably species of the genus *Spirulina* or any associated genus. It will be understood by those skilled in the art that each of the components of the polyculture perform differently, whereas some of the components may perform better in certain conditions than others. Accordingly, it will be understood by those skilled in the art that the composition and component ratios of the polyculture may change as climate and atmospheric conditions change, such that the optimal composition of the polyculture is formed based on the particular conditions during the time of formation.

Referring to FIG. 1, a growth system 10 for the cultivation of the polyculture comprises at least one growing tray or container 12, and more preferably a plurality of growing trays 12, for active and continuous growth of the polyculture. Preferably, a growth facility comprises multiple growth systems 10. The polyculture is grown until a sufficient aquatic plant-based biomass is achieved in at least one of the growing trays 12 and, more preferably, in all of the growing trays 12. Preferably, the growing trays 12 are arranged in a vertically-stacked and spaced-apart orientation. Specifically, each tray 12 is oriented in a substantially horizontally position, such that the longitudinal axis of each growing tray 12 is generally parallel to the ground surface or the supporting surface on which the growth system 10 is situated, and is vertically spaced apart from an adjacent tray 12. Thus, the growth system 10 has a modular and multi-tiered design, which supports scalability and facilitates cultivation of the polyculture at a relatively high yield per acre, particularly since the volume of growing trays 12 per acre of land is substantially increased relative to conventional growth systems.

The number of growing trays 12 included in the growth system 10 is variable dependent upon the particular size of the growth system 10 and the gasifier unit 42, described further below ans shown in FIGS. 3-4. In the present embodiment, each growing tray 12 has a height of approximately four to six inches, a width of approximately six to ten inches, and a depth of approximately two to four inches. However, it will be understood by those skilled in the art that the size and shape of the growing trays may vary in particular applications, depending upon the particular needs of the facility.

Each of the growing trays 12 contains water and the starting polyculture. The polyculture only requires a few inches of water for adequate growth. More preferably, in the present embodiment, each of the growing trays 12 preferably contains a water level of approximately three inches for optimal growth of the polyculture. However, it will be understood by those skilled in the art that the contents of the growing trays and the amounts of polyculture and water may vary in particular applications, depending upon the particular needs of the facility. Each growing tray 12 preferably holds an overall volume of approximately from five to ten gallons of water and polyculture. Preferably, the plurality of growing trays 12 are operated in succession.

A stream 16 of air is preferably continuously provided to the plurality of growing trays 12 by a blower 14, preferably at a low pressure and a high volume. Preferably, a predetermined amount of carbon dioxide is continuously mixed with the air stream 16 at an injection point 18 to form an air/carbon dioxide stream 20 which is passed through the system 10 and, more particularly, through the growing trays 12. Preferably, the carbon dioxide content of the stream 20 is approximately twice of that of atmospheric levels, and more particularly, is approximately in the range of one to two parts per trillion. However, it will be understood by those skilled in the art that the carbon dioxide concentration may vary in particular applications, depending upon the particular needs of the facility and the characteristics of the particular polyculture being cultivated. More particularly, the air and carbon dioxide stream 20 is passed over the polyculture, and the air creates a sufficient level of agitation so as to cause the stoma of the duckweed increase their uptake of carbon dioxide. Thus, a rapid growth mode is achieved by the growth system 10.

A water stream 22 is also preferably continuously provided to the plurality of growing trays 12, preferably by a pump 24. More particularly, in the present embodiment, the water stream 22 is continuously provided to the plurality of growing trays 12 at a relatively low flow rate of approximately one gallon per minute. However, it will be understood by those skilled in the art that the water flow rate may vary in particular applications, depending upon the particular needs of the facility and the characteristics of the particular polyculture being cultivated. More preferably, during spaced-apart periodic intervals, the plurality of growing trays 12 are provided with a higher flow of water, preferably a water stream 22 at a flow rate of approximately five to ten gallons per minute. More preferably, the higher flow rate intervals occur during periods of harvesting of the polyculture, as described below. The air/carbon dioxide stream 20 and the water stream 22 are preferably circulated throughout the growth system 10 in a closed loop system.

The pH of the water stream 22 is also preferably continuously monitored. More preferably, the pH of the water stream 22 is adjusted to and maintained at a pH suitable for growth of the polyculture into a biomass. Preferably, the pH of the water stream 22 is adjusted to and maintained at a pH of from approximately 6 to approximately 7. More preferably, the pH of the water stream 22 is adjusted to and maintained at a pH of 6.5.

The water stream 22 is preferably enriched with carbon dioxide for adjustment to and maintenance of the desired pH of the water stream 22. The carbon dioxide enriched water may be formed, for example, by bubbling carbon dioxide into the water by a micro bubbler (not shown). However, it will be understood by those skilled in the art that any enrichment process or system may be used for generation of a carbon dioxide-rich water stream 22.

Nutrients are preferably continuously pumped to and circulated through the growth system 10, and more particularly across each of the plurality of growing trays 12. The nutrients are preferably in the form of a compost tea solution (represented by stream 26) at a variable flow rate. The compost tea solution is a liquid solution or suspension made by steeping a compost mixture in oxygenated water. An aerobic compost tea brewing system 28 is preferably disposed adjacent or proximate to the growth system 10 for creation of the compost tea. However, it will be understood by those skilled in the art that the brewing system 28 may be located remotely from the growth system 10, as long as the compost tea can be pumped or otherwise conveyed to the growth system 10. The compost mixture used to produce the compost tea solution comprises primarily manure and other types of agricultural waste or biomass. It will be understood by those skilled in the art that virtually any composition or ratio of manure and agricultural waste or biomass may be utilized for creation of the compost tea solution. It will also be understood by those skilled in the art that any nutrients suitable for duckweed growth may be used for creation of the compost tea solution.

The aerobic compost tea brewing system 28 may be any type of currently available brewing system which sufficiently mixes the compost mixture with oxygenated water and air to stimulate the growth of microbes. Preferably, the compost tea brewing system 28 is provided with a predetermined amount of oxygenated water once or twice daily. The oxygenated water steeps in and passes through the compost mixture contained within the brewing system 28. The compost tea solution containing the nutrients is in the form of a leachate that exits from the brewing system. Preferably, the total dissolved solids content of the compost tea solution, and more particularly the total amount of available nutrients in the compost tea solution, is in the range of approximately 500 to 600 parts per million.

Preferably, the stream 26 of the compost tea solution is pumped directly from the brewing system 28 into the water stream 22, and is thus continuously provided to the growth system 10 in a closed loop system with the water. In another embodiment, a stream 32 (shown in phantom in FIG. 1) of the compost tea solution is preferably continuously provided to the plurality of growing trays 12 by a conduit 30 which extends from the brewing system 28 directly to the growth system 10. Thus, the compost tea solution is fed to the growth system 10 in a stream 32 which is separate from the water stream 22, and the compost tea solution is preferably recirculated to the brewing system 28 for the generation of more solution in a closed loop system.

By the continuous and closed loop recirculation of air, carbon dioxide, water and nutrients to the polyculture, preferably during a twenty four hour period on a daily basis, a continuous and rapid growth mode is achieved in the growth system 10. In the growth system 10, the growing trays 12 and, more particularly, the polyculture, benefits from illumination by a natural light source to promote more rapid growth. However, the polyculture is also preferably subjected to illumination by an artificial light source, which provides supplemental lighting for promoting growth of the polyculture. Preferably, the growth system 10 is illuminated by an artificial light source of the blue light spectrum. However, it will be understood by those skilled in the art that the necessary light intensity and spectrum will vary based on the particular duckweed species utilized.

The cultivation or growth phase of the process is continued until a desired quantity of mature polyculture specimens are produced, that is until a sufficient quantity of an aquatic plant-based biomass, and more particularly a duckweed-based biomass, is produced. Cultivation/growth times are determined empirically and vary, depending on numerous factors within the control of the operator including, for example, the identity of the duckweed species, the composition of the compost tea solution, the composition of the air/carbon dioxide feed stream 20, the pH of the water, the temperature of the water, and the light intensity within the growth system 10. Preferably, the polyculture is approximately doubled in body weight on a daily basis (i.e., every twenty four hours). Preferably, the typical life cycle of the polyculture in the growth system 10 is approximately three to four days.

Figure 2:
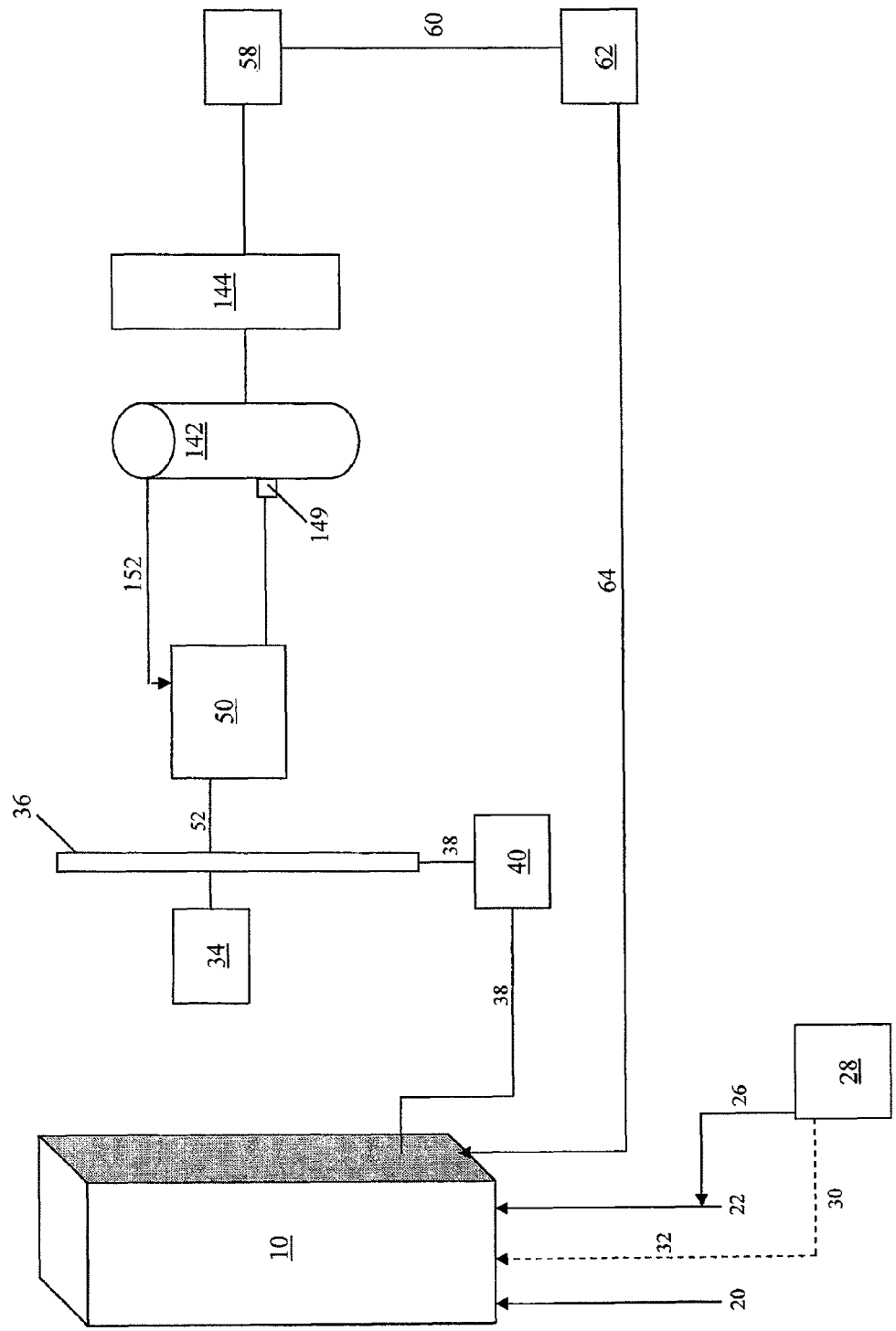
FIG. 2 is a schematic block diagram illustrating a process for producing aquatic-based biogas according to preferred embodiment of the present invention.

Referring to FIGS. 1-2, following growth of the polyculture within the growth system 10 into an aquatic plant-based biomass, a portion of the contents of the growing trays 12 (i.e., portions of the duckweed-based biomass) are withdrawn or harvested from the growth system 10. The harvesting activity is perfomed in an upflow mode, such that the duckweed-based biomass is harvested via a gravity flow system. Specifically, higher flow rates of water are preferably provided to the growth system 10 during periods of harvesting, such that the water level in the growing trays 12 is caused to rise, thereby resulting in the contents of the growing trays 12 overflowing from the growing trays 12. Preferably, the polyculture is withdrawn or harvested using a weir system in a manner known in the art. Also, as some of the polyculture specimens reach maturity, the mature plant specimens will naturally float to the top of each of the growing trays 12. A weir system thus skims off and withdraws such plant specimens from the growing trays 12. Therefore, a mixture of older and younger specimens are withdrawn during the harvesting process.

In the present embodiment, the predetermined fluid flow rate of the harvesting activity is preferably approximately four to six gallons per minute. However, it will be understood by those skilled in the art that the harvesting flow rate may vary in particular applications, depending upon the particular needs of the facility and the characteristics of the particular biomass. The harvesting activity preferably occurs at random intervals, but may alternatively occur at regular spaced-apart intervals. Also, the harvesting activity is preferably performed at an aggressive rate, since it has been found that aggressive harvesting simulates the stresses of nature generally imposed on duckweed plants and thereby results in increased growth of the duckweed.

Harvesting of a portion of the contents of the growth system 10 may be performed on a continuous basis until the desired percentage of approximately 20% to 40% of the contents of the growth system 10 are removed. Alternatively, the desired percentage of the contents may be removed all at once. The polyculture remaining in the growing trays 12 continues to grow, multiply and refill the growing trays 12, as additional enriched air, water, nutrients and carbon dioxide are introduced into the system 10.

The withdrawn aquatic biomass is then subjected to a collection and separation process. Preferably, the harvested or withdrawn duckweed-based biomass is sent by gravity flow to a collector 34, such as a collection tank, a standpipe, a hopper, and the like. For separation of the solid plant specimens from any residual liquids, such as water and compost tea, the collected specimens are passed through a filtration screen 36. The filtration screen 36 preferably has a mesh size of approximately 2 to 5 microns. However, it will be understood by those skilled in the art that any appropriate mechanical separation process may be utilized, as long as the solid plant particles are sufficiently separated from residual liquids. For example, the collected biomass may be separated into independent lots via an underwater air distribution system (not shown), or may be passed through a polyphasic separator.

The withdrawn or collected biomass (i.e., the retentate) is then pumped out of the growth system 10 via a conduit 52 and into a dryer 50 for drying of the aquatic biomass. Upon exiting the collection and separation system, the collected biomass typically has a moisture content of approximately 85%. Preferably, the dryer 50 reduces the moisture content of the collected biomass to approximately 50% moisture. The dryer 50 preferably includes a shaking table and a drying tunnel. Other examples of the type of drying equipment or processes which may be used include, but are not limited to a drying rack or desiccation. The dryer 50 is preferably powered by off-gases from the combustion zone 48, 148 of the gasifier 42, 142, described in more detail below and shown in FIGS. 3-5. The filtrate from the filtration process is conveyed to a sump 40, or other type of collection basin, via a recirculation conduit 38, and is ultimately circulated back into the growth system 10.

Referring to FIG. 2, the dried aquatic plant-based biomass, comprising the dried duckweed, algae and aquatic fern, is then subjected to a gasification process for conversion of the biomass into a biogas. More particularly, the dried aquatic biomass is pumped, or otherwise conveyed, to a dual-zone processor, such as a dual-zone gasifier. In the gasifier, the aquatic plant-based biomass, and more particularly the duckweed-based biomass, is subjected to pyrolysis and combustion processes.

Referring to FIGS. 3-4, there is shown a first preferred embodiment of a gasifier 42. The gasifier 42 comprises an inner chamber 46 and an outer chamber 48. The inner chamber 46 is a pyrolysis tube, preferably in the form of a coiled tube with an internal cavity 46a, which constitutes the pyrolysis zone of the gasifier 42. The outer chamber 48 is a combustion chamber which is preferably generally cylindrical in shape and constitutes the combustion zone of the gasifier 42. The inner chamber 46 and the outer chamber 48 are arranged, such that the inner pyrolysis tube 46 is located within the internal cavity 48a of the combustion chamber 48. Thus, the areas where the pyrolysis and combustion occur remain isolated and generally completely separated from each other. It will be understood by those skilled in the art that the outer chamber 48 may have virtually any shape, such a cube, a rectangular prism, and the like. It will also be understood by those skilled in the art that the gasifier 42 may comprise more than one pyrolysis tubes 46 arranged within the combustion chamber 48. In one embodiment, the gasifier 42 is supported by a plurality of supporting legs 49.

Figure 5:
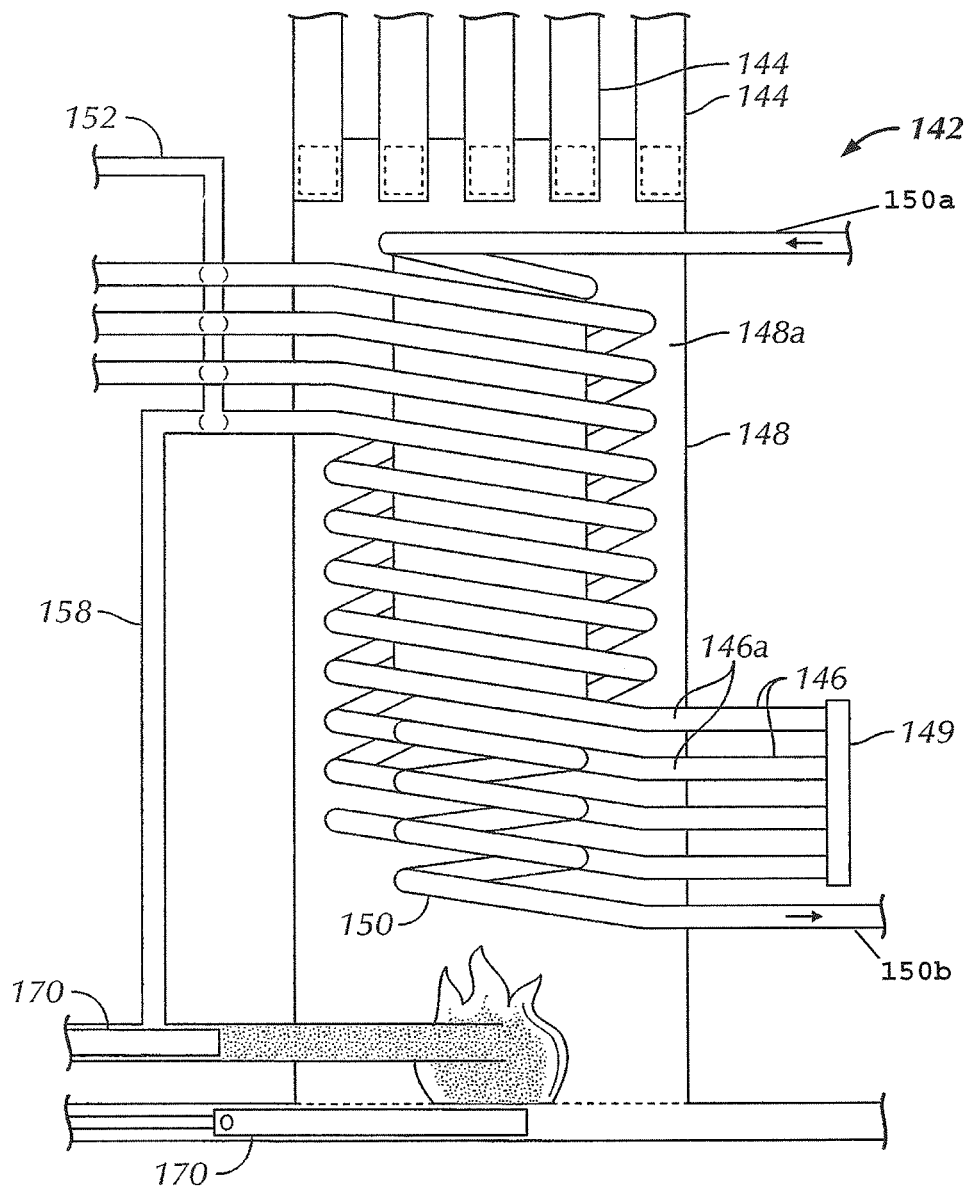
FIG. 5 is a partial side elevation view of a gasifier according to another preferred embodiment of the present invention, with a side panel of the gasifier being removed and the interior components being visible.
Figures 6, 7:
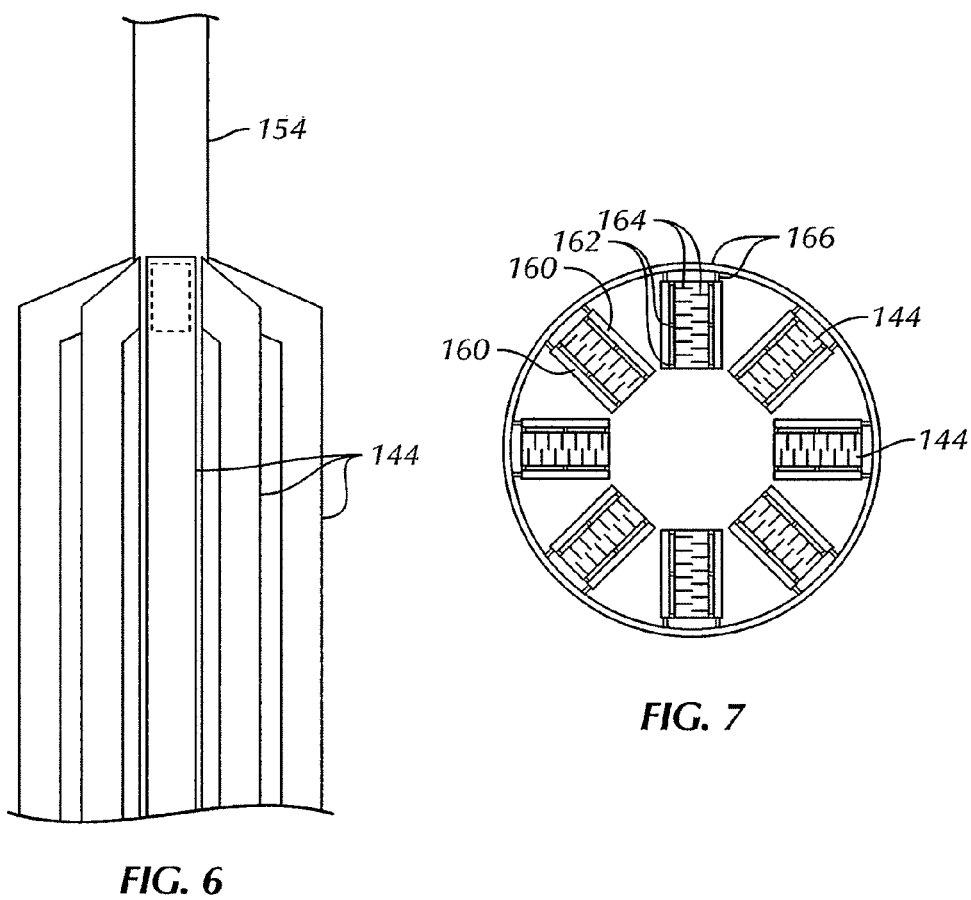
FIG. 6 is another partial side elevation view of the gasifier shown in FIG. 5.
FIG. 7 is a top plan view of a portion of the gasifier show in FIG. 5.

Referring to FIGS. 5-7, there is shown a second preferred embodiment of a vertically-oriented gasifier 142. The gasifier 142 comprises an inner pyrolysis tube 146, and more preferably a plurality of inner pyrolysis tubes 146, arranged in a coiled fashion within an interior cavity 148a of a combustion chamber 148. Both the pyrolysis tubes 146 and the combustion chamber 148 extend in a generally vertical direction. Each of the inner pyrolysis tubes 146 preferably has a diameter in the range of approximately one to two inches and preferably has a straight length in the range of approximately twenty-two to twenty-seven feet. More preferably, each inner pyrolysis tube 146 has a straight length of approximately twenty-five feet. The gasifier 142, and more particularly the combustion chamber 148, preferably has a diameter in the range of approximately five to seven feet and a height in the range of approximately four to six feet. More preferably, the combustion chamber 148 has a diameter of approximately six feet and a height of approximately five feet. However, it will be understood by those skilled in the art that the dimensions of the gasifier 142, and particularly of the pyrolysis tubes 146 and the combustion chamber 148, may easily be scaled up or down to suit the particular needs of the biogas facility at which the gasifier 142 is utilized.

The internal cavities 146a of the pyrolysis tubes 146 are packed, preferably continuously, with the duckweed-based biomass product and are maintained as an anaerobic environment. Preferably, each internal cavity 146a is continuously packed with a sufficient quantity of duckweed-based biomass so as to substantially completely suppress the presence of oxygen. Accordingly, after the drying process, the biomass is preferably conveyed directly into the pyrolysis zone 146. More preferably, the biomass is directly conveyed by a specifically designed screw auger to a manifold 149 of the plurality of pyrolysis tubes 146. The pyrolysis tubes 146 are then heated up to their operating temperature by the combustion zone. The gasifier 142 comprises a coiled water heating tube 150 for heating purposes. The coiled water heating tube 150 has an inlet 150a and an outlet 150b. More particularly, the combustion zone 148 of the gasifier 142 is preferably maintained at a temperature in the range of 1200° F. to 1800° F., and more preferably to a temperature of 1600° F., and is utilized to heat up the pyrolysis chamber 146 to a predetermined reaction temperature. The pyrolysis chamber 146 is preferably heated up to a temperature in the range of 1200° F. to 1800° F., and more preferably to a temperature in the range of 1300° F. to 1600° F., and most preferably to a temperature in the range of 1350° F. to 1600° F.

Since biomass is continuously fed into the pyrolysis tubes 146, the biomass is constantly moving through the pyrolysis tubes 146 during its dwell time in the gasifier 142. Preferably, pyrolysis of the biomass is achieved during the dwell time of the biomass within the pyrolysis tubes 148 within the gasifier 142. More specifically, pyrolysis of the biomass occurs at such temperatures for a duration of approximately twelve to twenty minutes, or until the supercritical reformation process and the reverse water gas shift reaction occur. Supercritical reformation of the biomass is achieved when the volatiles are released from the biomass, and more particularly from the carbon molecules of the biomass, thereby creating a biochar product and a plasma comprising carbon, hydrogen and oxygen molecules. The reverse water gas shift reaction is completed when the remaining components of the pyrolyzed biomass, and more particularly, the plasma, cool down and reform into a natural gas of a lower energy format. Specifically, the carbon, hydrogen and oxygen molecules reform into a biogas comprising mainly methane, as well as some hydrogen and carbon dioxide. The chlorophyll molecules of the aquatic biomass remain in suspension.

Typically, a biomass containing one pound of duckweed produces approximately three cubic feet of biogas and approximately 0.2 pounds of biochar. In the gasifier 142, the biogas production rate is in the range of approximately three to six cubic feet per second and the biochar production rate is in the range of approximately 0.2 to 0.4 pounds per second. However, it will be understood by those skilled in the art that the amounts of biogas and biochar which are produced depend upon the particular capacity and dimensions of the gasifier, which may be scaled up or down depending upon the particular needs of the biogas facility.

The biogas which is formed by the gasifiers 42, 142 is a high quality biogas with essentially no waste products. Since the combustion zone is isolated from the pyrolysis zone, where the natural gas is formed, the exhaust gases from the combustion zone do not contact and drive down the BTU value of the biogas. Moreover, no tar products are formed in the gasifiers 42, 142. Referring to FIGS. 2 and 5, in the gasifier of the second embodiment, the biogas exits the pyrolysis tubes 146, preferably by residual pressure, and is subsequently recovered in a plurality of collection chambers 144. The biogas exits the collection chambers 144 via a flue 154 and are cooled (see FIG. 6). Referring to FIG. 7, each of the collection chambers 144 comprises a plurality of coolant chambers 160, a plurality of thermoelectric generators 162, and a plurality of heat transfer studs 164. A coolant transfer tube 166 extends around the periphery of the plurality of the collection chambers 144. In another embodiment, the biogas may pass directly from the pyrolysis tubes 146 through a cooling tower (not shown) for removal of any residual solids.

The biochar is directed to the combustion zone 148 from the pyrolysis tubes 146 via a conduit 158 and is utilized as fuel for the combustion zone 148. The gasifier is powered by two hydraulic piston rams 170. The exhaust gases from the combustion zone exit the gasifier 142 via a conduit 152 and are subjected to a purification treatment, if necessary, and may be used to power the dryer 50. Any resulting carbon dioxide is recirculated to the growth system 10 for reuse and reprocessing.

The resulting biogas can then be utilized for various purposes. In particular, the duckweed-based and methane-containing biogas is of a sufficiently high quality to be utilized to drive steam turbines for the generation of electricity. The aquatic plant-based (i.e., duckweed-based) biogas may also be combusted in an internal combustion or spark-ignition engine 58 to generate useful energy. The exhaust gas from the internal combustion engine which combusts the duckweed-based biogas comprises carbon dioxide, water vapor, carbon monoxide and nitrogen oxide. The exhaust gas (represented by conduit 60 in FIG. 2) is passed through any type of conventional or commercially available catalyst 62 for the removal of the carbon monoxide gas. The remaining gases (i.e., the carbon dioxide, water vapor and nitrogen oxide represented by conduit 64) may then be recirculated to the growth system 10 for nourishment of the polyculture. Specifically, the cyanobacteria and the multiple species of the duckweed will consume the carbon dioxide and the water vapor as part of the life processes. The cyanobacteria will also consume portions of the carbon dioxide and the nitrogen oxide, and then convert these gases into nitrates and nitrites. The nitrates and nitrates, in turn, are fertilizers used by the duckweed species as nutrients. Thus, no nitrogen oxide, which is a pollutant, is entrained in the gas and no disposal or regeneration of catalysts is necessary. The system for converting duckweed into biogas is thus a closed loop and sustainable system.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for producing a biogas comprising
a plurality of growing containers containing water and a polyculture of aquatic plants, the polyculture comprising at least one species of duckweed, the plurality of growing trays being configured to continuously receive carbon dioxide and nutrients until a duckweed-based biomass is produced;
a harvesting system configured to harvest a portion of the duckweed-based biomass contained in at least one of the plurality of growing containers; and
a vertically-oriented gasifier comprising a pyrolysis chamber and a combustion chamber, the pyrolysis chamber comprising a plurality of coiled pyrolysis tubes arranged within an interior of the combustion chamber.

2. The system of claim 1, wherein the plurality of growing containers are arranged in a vertically stacked orientation with a space between each adjacent growing container.

3. The system of claim 1, wherein each coiled tube has a diameter in the range of approximately one to two inches and has a straight length of approximately twenty-two to twenty-seven feet.

4. The system of claim 1, wherein the pyrolysis chamber is maintained at a temperature range between 1200° F. and 1800° F.

5. The system of claim 1, wherein the combustion chamber has a diameter in the range of approximately five to seven feet and a height in the range of approximately four to six feet.

6. The system of claim 1, wherein the duckweed-based biomass is fed to each of the coiled pyrolysis tubes at a bottom end of the gasifier and travels through the plurality of coiled pyrolysis tubes in an upward direction toward an upper end of the gasifier, a biogas and a biochar being produced by the gasifier.

7. The system of claim 6, further comprising a plurality of collection chambers configured to store the biogas produced by the gasifier.

8. The system of claim 6, wherein the biochar is directed to the combustion chamber from the plurality of coiled pyrolysis tubes and is utilized as fuel for the combustion chamber.

* * * * *